(12) United States Patent
Boser et al.

(10) Patent No.: US 8,005,549 B2
(45) Date of Patent: *Aug. 23, 2011

(54) MEDICAL ELECTRICAL LEAD

(75) Inventors: Gregory A. Boser, Richfield, MN (US);
Kevin R. Seifert, Forest Lake, MN (US);
Greg Garlough, Bloomington, MN (US)

(73) Assignee: Medtronic, Inc., Minneapolis, MN (US)

( * ) Notice: Subject to any disclaimer, the term of this patent is extended or adjusted under 35 U.S.C. 154(b) by 288 days.

This patent is subject to a terminal disclaimer.

(21) Appl. No.: 12/211,065

(22) Filed: Sep. 15, 2008

(65) Prior Publication Data

US 2009/0076577 A1    Mar. 19, 2009

Related U.S. Application Data

(60) Provisional application No. 60/972,114, filed on Sep. 13, 2007, provisional application No. 60/973,479, filed on Sep. 19, 2007.

(51) Int. Cl.
*A61N 1/05* (2006.01)
(52) U.S. Cl. ........................................... 607/116
(58) Field of Classification Search ........... 607/115–116
See application file for complete search history.

(56) References Cited

U.S. PATENT DOCUMENTS

| | | | |
|---|---|---|---|
| 5,358,516 A * | 10/1994 | Myers et al. | 607/116 |
| 5,393,929 A | 2/1995 | Yagihashi | |
| 5,935,159 A | 8/1999 | Cross, Jr. et al. | |
| 7,519,432 B2 | 4/2009 | Bolea et al. | |
| 2004/0167595 A1 | 8/2004 | Tuominen | |
| 2005/0103518 A1 | 5/2005 | Glew | |
| 2005/0137671 A1 | 6/2005 | Liu et al. | |
| 2006/0089691 A1 | 4/2006 | Kaplan et al. | |
| 2006/0265037 A1 * | 11/2006 | Kuzma | 607/116 |
| 2007/0250143 A1 * | 10/2007 | Sommer | 607/116 |

FOREIGN PATENT DOCUMENTS

| | | |
|---|---|---|
| JP | 410149728 A | 6/1998 |
| WO | 9829055 | 7/1998 |
| WO | 0191851 | 12/2001 |

OTHER PUBLICATIONS

U.S. Appl. No. 12/211,093, filed Sep. 15, 2008, entitled "Medical Electrical Lead".
U.S. Appl. No. 12/211,070, filed Sep. 15, 2008, entitled "Medical Electrical Lead".
U.S. Appl. No. 12/211,075, filed Sep. 15, 2008, entitled "Medical Electrical Lead".

(Continued)

*Primary Examiner* — Carl H Layno
*Assistant Examiner* — Jessica Sarcione
(74) *Attorney, Agent, or Firm* — Reed A. Duthler; Stephen W. Bauer

(57) ABSTRACT

A method of manufacture of a medical device lead. The lead includes one or more jacketed conductive elements. The jacket comprises one or more covers. The jacketed conductive element is formed by introducing a polymeric material over a conductive element, coupling the conductive element around a mandrel to form a coil shape, annealing the polymeric material over the at least one conductive element and setting a coiled shape in the at least one conductive element; and then removing the at least one conductive element from the mandrel.
The coiled conductive element as manufactured thus substantially retains its original coiled shape.

9 Claims, 12 Drawing Sheets

OTHER PUBLICATIONS

U.S. Appl. No. 12/211,092, filed Sep. 15, 2008, entitled "Medical Electrical Lead".
U.S. Appl. No. 12/211,096, filed Sep. 15, 2008, entitled "Medical Electrical Lead".
International Search Report and Written Opinion of international application No. PCT/US2008/010788, mailed Feb. 18, 2009, 11 pp.
International Search Report and Written Opinion of international application No. PCT/US2008/010787, mailed Mar. 3, 2009, 11 pp.
International Search Report and Written Opinion of international application No. PCT/US2008/010786, mailed Mar. 3, 2009, 11 pp.
International Search Report and Written Opinion of international application No. PCT/US2008/010789, mailed Jul. 20, 2009, 15 pp.
International Search Report and Written Opinion of international application No. PCT/US2008/010781, mailed Feb. 18, 2009, 11 pp.
International Search Report and Written Opinion of international application No. PCT/US2008/010785. mailed Feb. 18, 2009, 11 pp.
Office Action from U.S. Appl. No. 12/211,096 dated Jun. 8, 2010, 12 pp.
International Preliminary Report on Patentability from PCT Application No. PCT/US2008/010788, issue date Mar. 16, 2010, 7 pp.
International Preliminary Report on Patentability from PCT Application No. PCT/US2008/010789, issue date Mar. 16, 2010, 9 pp.

\* cited by examiner

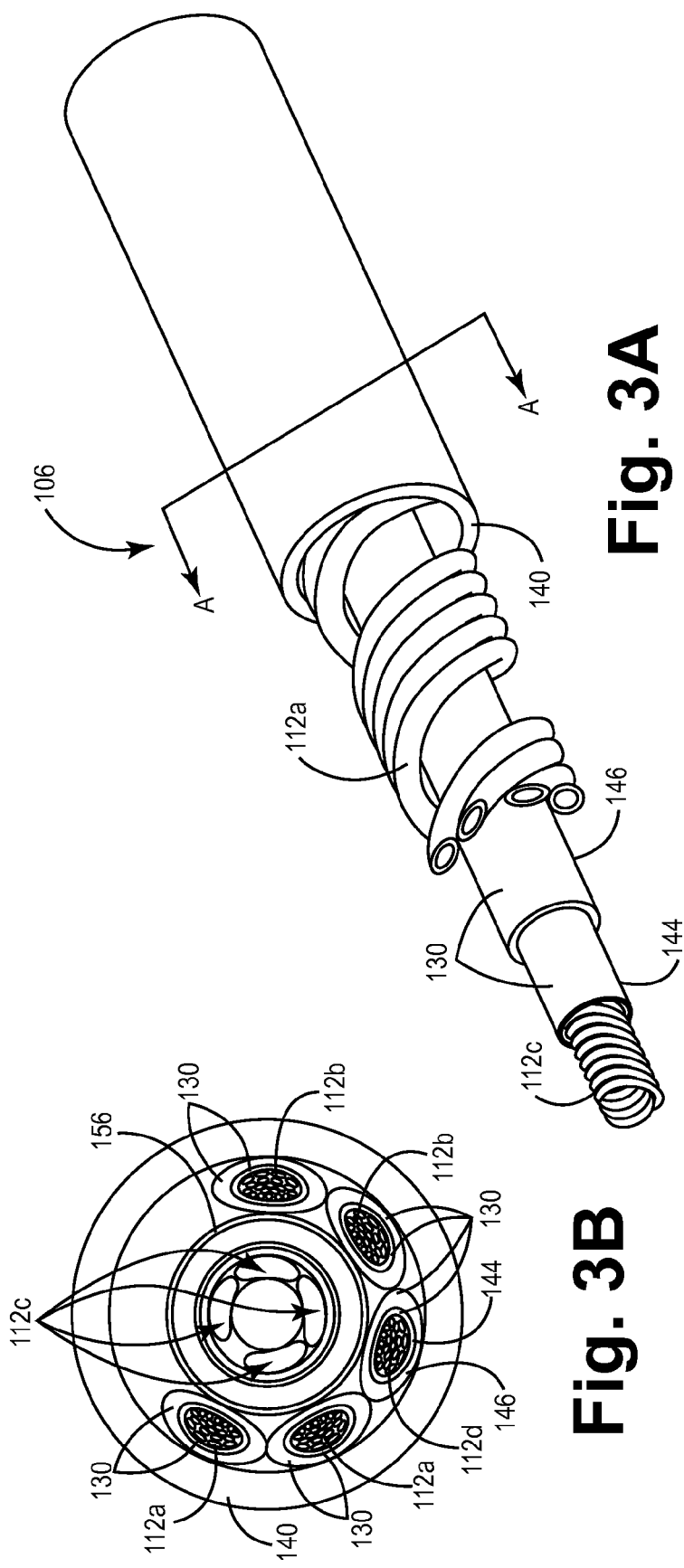

MEDICAL ELECTRICAL LEAD

CROSS-REFERENCE TO RELATED APPLICATION

The present application claims priority and other benefits from U.S. Provisional Patent Application Ser. No. 60/973,479 filed Sep. 19, 2007, incorporated herein by reference in its entirety. The present application also claims priority and other benefits from U.S. Provisional Patent Application Ser. No. 60/972,114 filed Sep. 13, 2007, incorporated herein by reference in its entirety.

TECHNICAL FIELD

The disclosure relates to implantable medical devices and, more particularly, to implantable medical leads.

BACKGROUND

The human anatomy includes many types of tissues that can either voluntarily or involuntarily, perform certain functions. After disease, injury, or natural defects, certain tissues may no longer operate within general anatomical norms. For example, after disease, injury, time, or combinations thereof, the heart muscle may begin to experience certain failures or deficiencies. Certain failures or deficiencies can be corrected or treated with implantable medical devices (IMDs), such as implantable pacemakers, implantable cardioverter defibrillator (ICD) devices, cardiac resynchronization therapy defibrillator devices, or combinations thereof.

IMDs detect and deliver therapy for a variety of medical conditions in patients. IMDs include implantable pulse generators (IPGs) or implantable cardioverter-defibrillators (ICDs) that deliver electrical stimuli to tissue of a patient. ICDs typically comprise, inter alia, a control module, a capacitor, and a battery that are housed in a hermetically sealed container with a lead extending therefrom. It is generally known that the hermetically sealed container can be implanted in a selected portion of the anatomical structure, such as in a chest or abdominal wall, and the lead can be inserted through various venous portions so that the tip portion can be positioned at the selected position near or in the muscle group. When therapy is required by a patient, the control module signals the battery to charge the capacitor, which in turn discharges electrical stimuli to tissue of a patient through via electrodes disposed on the lead, e.g., typically near the distal end of the lead. Typically, a medical electrical lead includes a flexible elongated body with one or more insulated elongated conductors. Each conductor electrically couples a sensing and/or a stimulation electrode of the lead to the control module through a connector module. It is desirable to develop implantable medical electrical leads with new lead body subassemblies.

BRIEF DESCRIPTION OF DRAWINGS

Aspects and features of the present invention will be appreciated as the same becomes better understood by reference to the following detailed description of the embodiments of the invention when considered in connection with the accompanying drawings, wherein:

FIG. 3A is a schematic view of a distal end of the medical electrical lead;

FIG. 3B is a cross-sectional view taken along plane A-A of the distal end of the medical electrical lead depicted in FIG. 3A;

DETAILED DESCRIPTION

Figure 1:
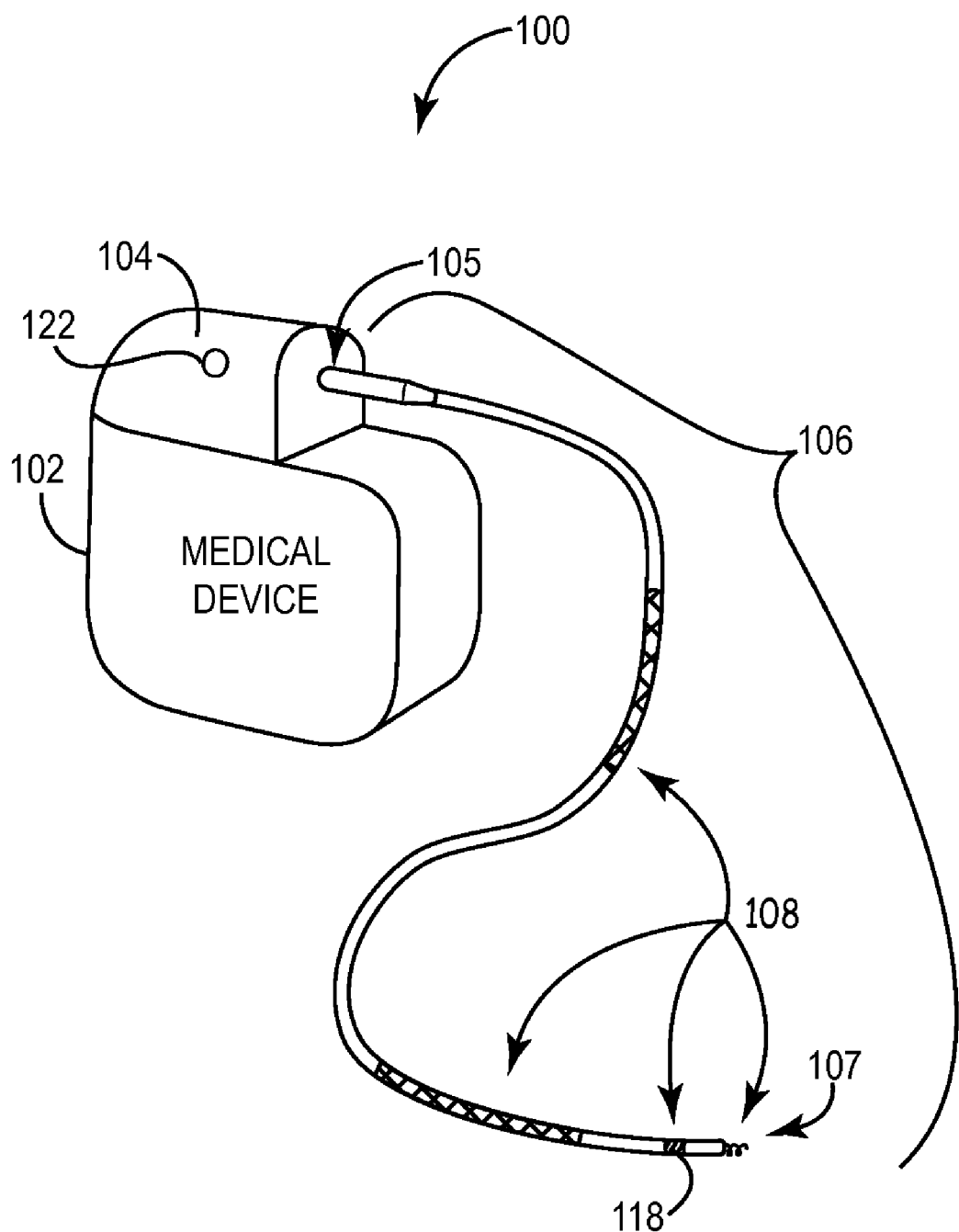
FIG. 1 is a conceptual schematic view of an implantable medical device in which a medical electrical lead extends therefrom.

The present disclosure relates to a medical electrical lead that includes a lead body. The lead body comprises at least one elongated conductive element, such as a cable, surrounded by an elongated jacket. The jacket can include one or more covers. The jacket can be formed through an extrusion process directly over the conductive element, which reduces or eliminates diametrical expansion of the coiled conductive element which can occur due to elastic "springback" or stress relaxation of the coiled composite structure. A first cover comprises polyetherether ketone (PEEK) extruded directly over the conductive element. In one embodiment, the conductive element and the jacket, is then formed into a coil.

In another embodiment, a jacket or one or more longitudinal elements are formed by a first cover of PEEK that is directly adjacent to a conductive element. A second cover of polymeric material is placed over the first cover. The second cover comprises a polymer such as PEEK, ethylene-tetrafluoroethylene (ETFE), e-beam cross-linked ETFE, fluorinated ethylene propylene (FEP), perfluoroalkoxy (PFA), ethylene-tetraflouroethylene based copolymer (EFEP), silicone, polyurethane, or polyurethane-silicone copolymers.

In one embodiment, the PEEK undergoes a molecular mobility process prior to or during introduction of the PEEK over an elongated conductive element. Exemplary molecular mobility processes can include thermal annealing, stress relieving, or other suitable means for a material to achieve a more flexible molecular structure.

Thermal processing can involve exposing the composite structure to a controlled heating and cooling schedule. Suitable temperatures can depend upon the type of polymeric material and/or number of covers or layer(s) employed, to form a jacket, a composite jacket, or one or more longitudinal elements that can house conductive elements. PEEK, for example, can be thermally processed at about 130-200 degrees Celsius (° C.). Thermal processing of PEEK onto an elongated conductive element causes the conductive element to substantially maintain a controlled pitch and diameter after coiling. For example, a conductive element such as a cable in a coil shape can substantially maintain up to about 99 percent of its original coil shape, after the conductive element has been released from, for example, a mandrel which is after a thermal processing has been performed. The final diameter and pitch of a coil shape is generally based upon the coil composite structure and its elastic "springback" or coil expansion from stress relaxation, the winding diameter/pitch, and the processing parameters used to set the coil shape. In one embodiment, a coiled cable is more resistant to flex fatigue compared to a linear or straight cable. Additionally, smaller coiled cable diameters are achieved through application of the principles described herein. In one embodiment, about 10 percent or more of a diameter reduction in the coiled conductive element is achieved through the principles described herein. In another embodiment, about 5 percent or more diameter reduction is achieved in the coiled conductive element through the principles described herein. In still yet another embodiment, about 2 percent or more diameter reduction is achieved in the coiled conductive element through the principles described herein. Smaller coiled cable diameters allow for smaller sized leads to be produced. Smaller sized leads can include 7 French or smaller. In another embodiment, smaller sized leads can include 6 French or smaller. In still yet another embodiment, smaller sized leads can include 5 French or smaller. Reduction in coiled cable diameters and the lead body size through the use of extruded PEEK was unexpected since it is desirable to attain thin polymeric walls and PEEK, a material that possesses a relatively high melting point, a high modulus, and is very viscous, can be difficult to extrude, compared with most other thermoplastic polymers.

The principles described herein are applicable to all types of medical electrical leads. For example, the disclosure applies to cardiovascular leads (e.g. high voltage leads, low voltage leads etc.), neurological leads, or other suitable applications.

FIG. 1 depicts a medical device system 100. A medical device system 100 includes a medical device housing 102 having a connector module 104 (e.g. international standard (IS)-1, defibrillation (DF)-1, IS-4 etc.) that electrically couples various internal electrical components housed in medical device housing 102 to a proximal end 105 of a medical electrical lead 106. A medical device system 100 may comprise any of a wide variety of medical devices that include one or more medical lead(s) 106 and circuitry coupled to the medical electrical lead(s) 106. An exemplary medical device system 100 can take the form of an implantable cardiac pacemaker, an implantable cardioverter, an implantable defibrillator, an implantable cardiac pacemaker-cardioverter-defibrillator (PCD), a neurostimulator, a tissue and/or muscle stimulator. IMDs are implanted in a patient in an appropriate location. Exemplary IMDs are commercially available as including one generally known to those skilled in the art, such as the Medtronic CONCERTO™, SENSIA™, VIR- TUOSO™, RESTORE™, RESTORE ULTRA™, sold by Medtronic, Inc. of Minnesota. Non-implantable medical devices or other types of devices may also utilize batteries such as external drug pumps, hearing aids and patient monitoring devices or other suitable devices. Medical device system 100 may deliver, for example, pacing, cardioversion or defibrillation pulses to a patient via electrodes 108 disposed on distal end 107 of one or more lead(s) 106. Specifically, lead 106 may position one or more electrodes 108 with respect to various cardiac locations so that medical device system 100 can deliver electrical stimuli to the appropriate locations.

Figure 2:
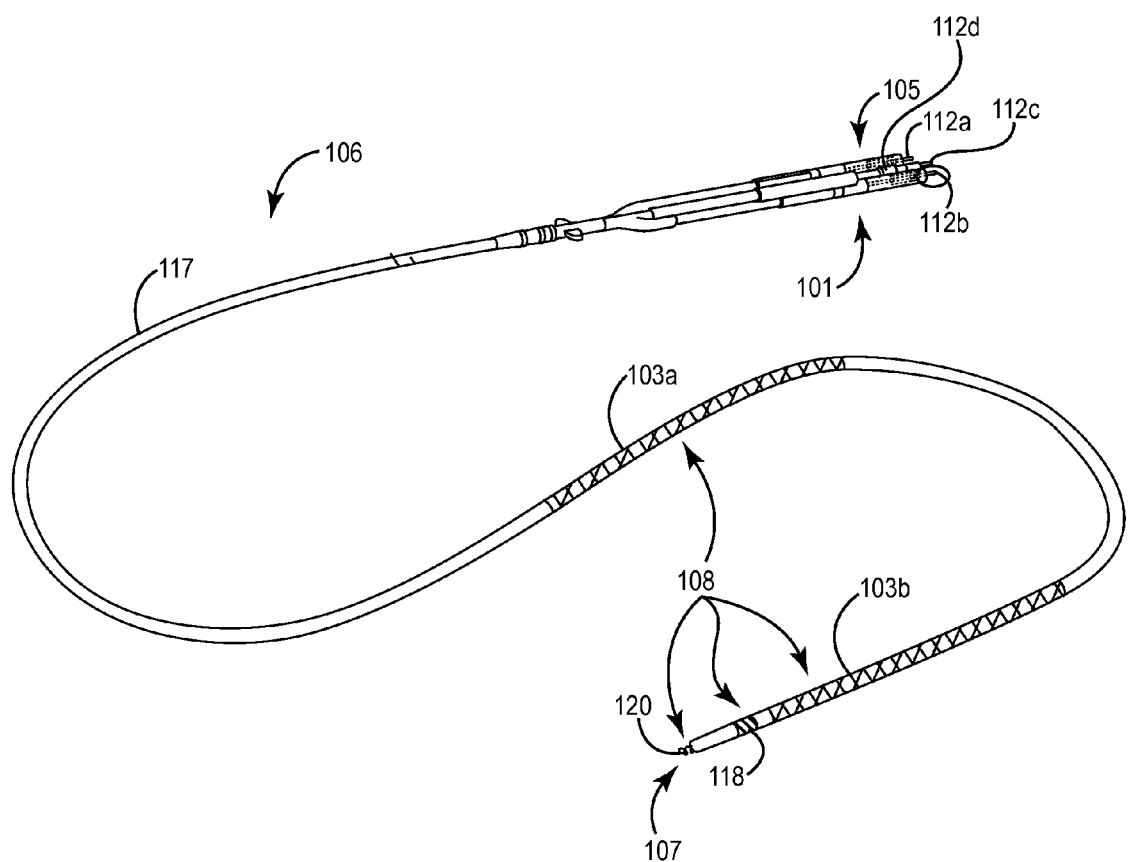
FIG. 2 is a schematic view of a medical electrical lead.

FIG. 2 depicts lead 106. Lead 106 includes a lead body 117 that extends from proximal end 105 to a distal end 107. Lead body 117 can include one or more connectors 101, and one or more jacketed conductive elements 112a-d. A jacket (also referred to as a liner, longitudinal element, coating) extends along and longitudinally around the conductive elements 112a-d and can serve to contain or mechanically constrain one or more conductive elements 112a-d. A jacket can also insulate one or more conductive elements 112a-d. Connector module 104 can contain connectors 122, such as set screws, serve to electrically and mechanically connect conductive elements 112a-d to ports (not shown) of connector module 104. Conductive element 112c (also referred to as a "conductor coil," "torque coil", "distal tip conductor") can extend to the distal end 107 and can optionally be coupled to a retractable and/or extendable helical tip. One or more conductive elements 112a,b serve as, or are connected to, defibrillation coils 103a,b that deliver electrical stimuli, when necessary, to tissue of a patient. Lead 106 can also include a conductive element 112d that extends from the proximal end 105 to ring electrode 118 while another conductive element 112c extends from proximal end 105 to tip electrode 120.

Electrically conductive elements 112a-d can include coils, wires, coil wound around a filament, cables, conductors or other suitable members. Conductive elements 112a-d can comprise platinum, platinum alloys, titanium, titanium alloys, tantalum, tantalum alloys, cobalt alloys (e.g. MP35N, a nickel-cobalt alloy etc.), copper alloys, silver alloys, gold, silver, stainless steel, magnesium-nickel alloys, palladium, palladium alloys or other suitable materials. Electrically conductive element 112a-d is covered, or substantially covered, longitudinally with a jacket 130 (also referred to as a liner, a longitudinal element, a longitudinal member, a coating, a tubular element, a tube or a cylindrical element). In yet another embodiment, each conductive element 112a-d is surrounded by a tubular element, which can possess a circular or a non-circular cross-section. An outercover or outerjacket in a lead body 117 can exhibit a non-circular cross-section.

Typically, the outer surface of electrodes 108 such as the ring electrode 118, the tip electrode 120, and the defibrillation coils 103a,b are exposed or not covered by a jacket 130 or liner so that electrodes 108 can sense and/or deliver electrical stimuli to tissue of a patient. A sharpened distal tip (not shown) of tip electrode 120 facilitates fixation of the distal end of helically shaped tip electrode 120 into tissue of a patient.

Referring to FIGS. 3A-3B, and 4A-4B, lead body 117 can include one or more jackets 130 and one or more conductive elements 112a,bd. In one embodiment, lead body 117 comprises one or more jackets 130 disposed in another jacket 130. In still yet another embodiment, lead body 117 comprises one or more jackets 130 with an outer cover 140 that surrounds the one or more jackets 130.

Figure 4A:
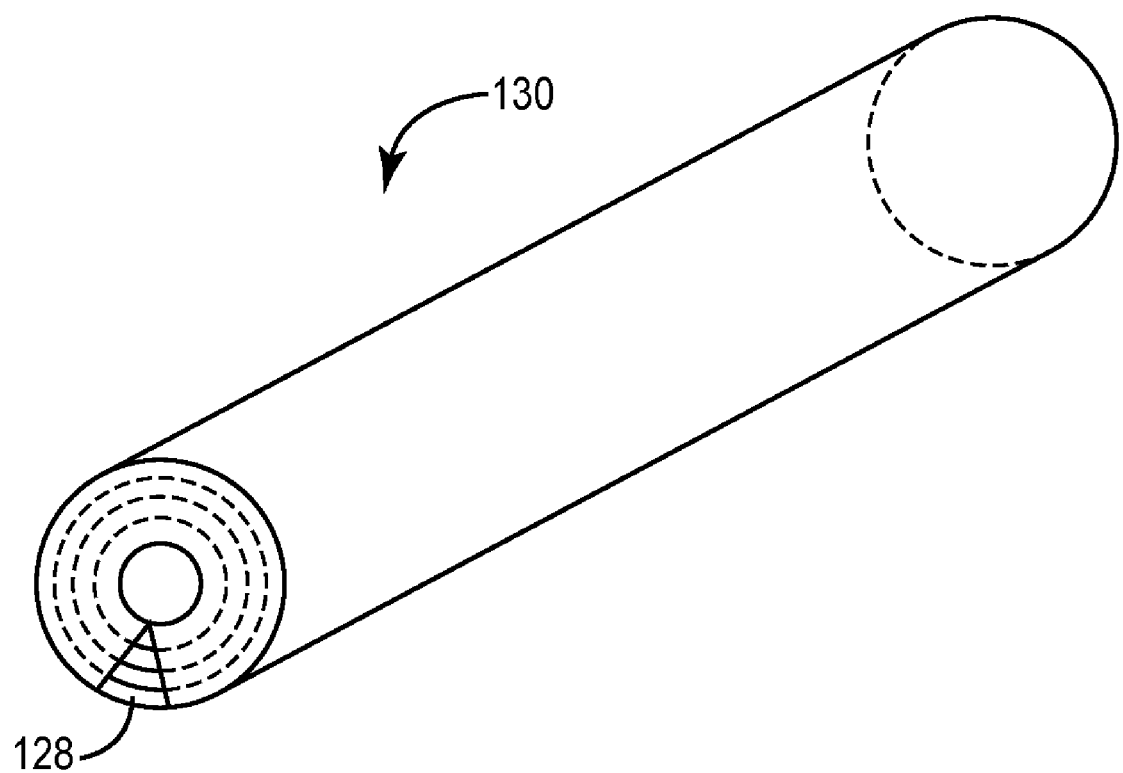
FIG. 4A is a schematic view of a jacket that surrounds one or more conductive elements in a medical electrical lead.
Figure 4B:
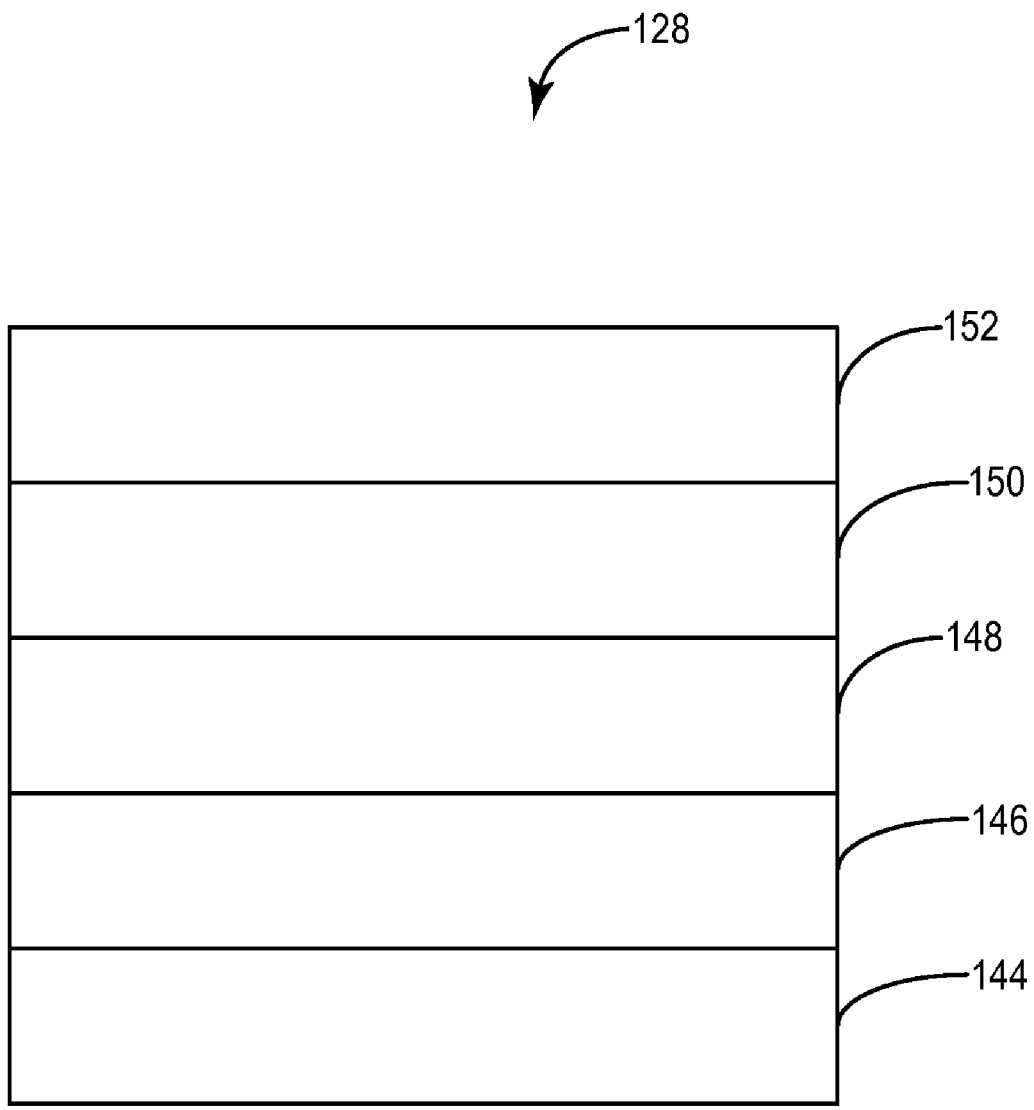
FIG. 4B is a schematic sectional view of the jacket depicted in FIG. 4A.

Each jacket 130 can include one or more covers, as depicted in FIGS. 4A-4B with cross-sectional segment 128. Each cover 146, 148, 150, and 152 can comprise one or more layers of polymeric compounds. Numerous embodiments of jacket 130 or liner are summarized in Table 1 and described in greater detail below. The first embodiment listed in Table 1 involves a single cover or first cover 144 of PEEK such that the inner lumen of first cover 144 is adjacent to a conductive element 112 a,b,d, a delivery device (not shown) such as a guide wire or stylet, or a lumen without a delivery device, or a conductive element 112c such as a conductor coil. PEEK is commercially available as Optima from Invibio located in Lancashire, United Kingdom. The first cover 144 of PEEK can be formed in a variety of ways. In one embodiment, the single cover or first cover of PEEK may be introduced or applied directly over a conductive element 112a-d through extrusion. Extrusion is the process of forming a continuous shape by applying force to a material through a die. Polymer extrusion is described, for example, in Chris Rauwendaal, pp. 1-30, 155-205, *Polymer Extrusion* (4$^{th}$ ed. 2001), which is incorporated by reference in relevant part. Generally, the polymeric material is heated in a barrel of the extruder until it attains or exceeds its melt temperature. Thereafter, the polymeric material is simultaneously extruded through a die of the extruder over the conductive element 112a-d while the conductive element 112a-d continues to move away from the extruder and/or the conductive element 112a-d moves radially. The polymeric material then forms into a first cover 144 (also referred to as first longitudinal element) over the conductive element 112a-d. After formation of first cover 144, the polymeric material is allowed to cool. There are numerous ways to cool the polymeric material. For example, the first cover 144 can be air cooled, which is a slow cooling process. Alternatively, the first cover 144 can be placed in a cool water bath. In yet another embodiment, the first cover 144 and the conductive element 112a-d can be placed into a cooler such as a refrigeration unit to quickly cool the polymeric material. The process of extruding polymeric material and allowing the polymeric material applies to each embodiment listed below.

The cover of PEEK can have a thickness of about 0.0005 inches to about 0.0015 inches. In another embodiment, the cover of extruded PEEK can possess a thickness that ranges from about 0.00020 inches to about 0.0012 inches. In yet another embodiment, the cover of PEEK has a thickness of about 0.0005 inches to about 0.0020 inches. The PEEK in combination with the conductive element 112a-d forms a composite structure.

The composite structure is then formed into a coil shape. In one embodiment, the composite structure is formed into a coil through, for example, winding the conductive element 112a, b,d over a mandrel 702, a cylindrically shaped element, exemplarily depicted in FIG. 10A. In particular, the mandrel 702 can be a high tensile strength wire that is held under tension (i.e. both ends of the mandrel 702 are clamped) while the filars of the coil are wound around the diameter of the mandrel 702. While the mandrel 702 continues to rotate or move radially, filars of the coil are being wound or served around mandrel 702. The filars are simultaneously translated along mandrel 702 while being wound about mandrel 702. An exemplary amount of winding tension applied is about 15 grams; however, it is appreciated that other amounts of winding tensions can be used The amount of tension used can depend upon the geometry and/or the mechanical characteristics (e.g. break load or strength of the cable filars, yield strength of the cable filars, etc.) of the cable filars that are to be formed. Coil winding equipment is commercially available from Accuwinder Engineering Company located in San Dimas, Calif.

The coiled conductive element 112a, b,d can be mechanically constrained to minimize or eliminate diametrical and/or axial expansion of the coiled conductive element 112a, b,d. Exemplary methods for mechanically constraining the conductive element 112a,b,d can include clamping or bonding the proximal and distal ends of 112a,b,d to a mandrel 702 or other suitable fixture or component. The clamp(s) or clamp mechanism(s) can mechanically constrain or secure the coiled conductive element 112a,b,d against the mandrel 702, as depicted, for example, in FIG. 10 such that coiled conductive element 112a,b,d will not rotate or expand diametrically and/or axially. Exemplary clamping mechanisms can take the form of a mechanical clamp, toggle(s) or heat shrink tubing(s). The clamping mechanism can mechanically constrain the coil conductive element on the mandrel and hold the coiled conductive element in place during subsequent operations.

In one embodiment, after the extrusion coating process and the coiling process, no thermal processing is performed on the coiled conductive element 112a, b,d. In another embodiment, after the extrusion coating process and the coiling process, thermal processing is performed on the coiled conductive element 112a, b,d. In still yet another embodiment, after the extrusion coating process, thermal processing is performed on the conductive element 112a, b,d which is thereafter followed by a coiling process to coil the conductive element 112a, b,d. In yet another embodiment, after the extrusion coating process, the coiled conductive element 112a, b,d is thermal processed and can then undergo a coiling process. After coiling process, the coiled conductive element 112a, b,d undergoes a second thermal process.

The composite structure can then undergo a thermal process; however, it is appreciated that a thermal process may be unnecessary to form, for example, a coiled cable assembly. In one embodiment, the composite structure is placed or run through a chamber. For example, a chamber or oven, commercially available from Despatch Industries, Minneapolis, Minn., can be used to process the composite structure. In one embodiment, the temperature in the chamber is about 130° C. to about 210° C. In one embodiment, the temperature in the chamber is about 130° C. to about 210° C. The composite structure remains at this temperature for about 30 seconds to about 45 minutes and then is cooled to form the PEEK polymeric material and conductive element 112a,b,d in its coiled shape. The mechanical constraint is then removed such as through de-clamping or cutting the proximal and distal ends of the conductive element 112 from the mandrel.

The second embodiment listed in Table 1 involves a first and a second cover of PEEK. First and second covers 144, 146, respectively, each possess a thickness of about 0.0005 inches to about 0.0015 inches of extruded PEEK. In another embodiment, first and second covers 144, 146, respectively, each possess a thickness of about 0.00020 inches to about 0.0012 inches. For this embodiment, the first cover of PEEK is formed by extruding the PEEK over a conductive element 112a,b,d. After the first cover 144 of PEEK has been formed, a second cover 146 is created by extruding PEEK over the first cover 144. In this embodiment, the composite structure, composed of the first and second covers of PEEK over the conductive element 112a,b,d, is then formed into a coil, as previously described.

The third embodiment involves a first, second, and third cover 144, 146, 148 of PEEK, respectively. First, second, and third covers 144, 146, 148 respectively, each possess a thickness of about 0.0005 inches to about 0.0015 inches of extruded PEEK. In another embodiment, first, second, and third covers 144, 146, 148 respectively, each possess a thickness of about 0.00020 inches to about 0.001 inches. In one embodiment, the first cover 144 of PEEK is formed by extruding the PEEK over a conductive element 112a,b,d. After the PEEK has formed or solidified, PEEK is extruded over the first cover 144 of PEEK to form a second cover 146 of PEEK. PEEK is extruded again over the second cover 146 to form a third cover 148 of PEEK. The composite structure composed of the first, second and third covers of PEEK over the conductive element 112a,b,d is then formed into a coil and mechanically constrained. The composite structure can then undergo a process such as thermal annealing or stress relieving. In one embodiment, the composite structure is placed in a chamber in which thermal annealing or a stress relieving process is applied to the composite structure. The temperature is raised to about 130° C. to about 210° C. for about 30 seconds to about 30 minutes to allow the PEEK polymeric material over the conductive element 112a,b,d to anneal or stress relieve original coil shape and encase conductive element 112a,b,d. The first, second and third covers 144, 146, 148 cool over the conductive element 112a,b,d, after which time the mechanical constraint is removed from conductive element 112a,b,d.

The fourth embodiment listed in Table 1 involves a first cover 144 of PEEK followed by a second cover 146 of ETFE. ETFE is understood to be commercially available from suppliers such as Daikin of Osaka, Japan and Asahi Glass Company of Japan; however, it is understood that for purposes of reading Table 1, other embodiments can include e-beam cross-linked ETFE.

A first cover 144 of PEEK can possess a thickness that ranges from about 0.0005 inches to about 0.0015 inches of extruded PEEK. In another embodiment, the first cover can possess a thickness of about 0.00020 inches to about 0.0020 inches and the second cover 146 can possess a thickness of about 0.00020 inches to about 0.00030 inches. In one embodiment, the first cover 144 of PEEK is formed by extruding the PEEK over a conductive element 112a,b,d. After the PEEK has formed, ETFE is extruded or wrapped over the first cover 144 of PEEK to form a second cover 146 of ETFE. A composite structure is formed of the first, and second covers 144, 146 over the conductive element 112a,b,d. The composite structure is then formed into a coil, as previously described. In an additional embodiment, the composite structure is wound on a mandrel coated with a polymer material that can thermally fuse to the outer most layer 146 of the composite structure to mechanically constrain selective regions or the entire coil length.

The fifth embodiment listed in Table 1 involves a first and a second cover 144, 146 of PEEK followed by a third cover 148 of ETFE. First and second covers 144, 146, respectively, each possess a thickness of about 0.0005 inches to about 0.0015 inches of extruded PEEK. In another embodiment, first and second covers 144, 146, respectively, each possess a thickness of about 0.00020 inches to about 0.001 inches. For this embodiment, the first cover 144 of PEEK is formed by extruding the PEEK over a conductive element 112a,b,d. After the first cover 144 of PEEK has been formed, a second cover 146 is formed by extruding PEEK over the first cover 144. The third cover 148, comprising ETFE, can then be extruded over the second cover 146. The composite structure is composed of the first, second, and third covers 144, 146, and 148, respectively and conductive element 112a,b,d. The composite structure is formed into a coil shape and then mechanically constrained, as previously described.

The composite structure can then undergo thermal annealing or stress relieving in a chamber, as previously described. The temperature in the chamber ranges from about 130° C. to about 210° C. for about 30 seconds to about 30 minutes to allow the polymeric material to form jacket 130 over conductive element 112a,b,d, after which time the mechanical constraint is removed.

The sixth embodiment involves a first, second, third and a fourth cover 144, 146, 148, 150. First, second, and third covers 144, 146, 148 comprise PEEK whereas the fourth cover 150 comprises ETFE. First, second, and third covers 144, 146, 148 respectively, each possess a thickness of about 0.0005 inches to about 0.0015 inches of extruded PEEK. In another embodiment, first, second, and third covers 144, 146, 148 respectively, each possess a thickness of about 0.00020 inches to about 0.001 inches. For this embodiment, the first cover of PEEK is formed by extruding the PEEK over a conductive element 112a,b,d. After the first cover 144 of PEEK has been formed, a second cover 146 is formed by extruding PEEK over the first cover 144. The third cover 148, comprising PEEK, can then be extruded over the second cover 146. The fourth cover 150, comprising ETFE, can then be extruded or wrapped over the third cover 148. The composite structure is composed of the first, second, third, and fourth covers 144, 146, 148, 150 respectively, over the conductive element 112a,b,d. The composite structure is formed into a coil shape and then mechanically constrained, as previously described.

The composite structure can then be placed into a chamber where the composite structure undergoes thermal annealing or stress relieving, as previously described. The temperature is raised to about 130° C. to about 210° C. for about 30 seconds to about 30 minutes to allow the polymeric material to encase conductive element 112a,b,d. The polymeric material is then allowed to form a jacket 130 over the conductive element 112a,b,d, after which time the mechanical constraint is removed.

The seventh embodiment involves a first, second, a third and a fourth cover 144, 146, 148, 150. First and second covers 144, 146 comprise PEEK whereas third and fourth covers 148, 150 comprise ETFE. Each cover 144, 146, 148, and 150 respectively, can possess a thickness that ranges from about 0.0005 inches to about 0.0015 inches. In another embodiment, first and second covers 144, 146, respectively, each possess a thickness of about 0.00020 inches to about 0.001 inches. For this embodiment, the first cover of PEEK is formed by extruding the PEEK over a conductive element 112a,b,d. After the first cover 144 of PEEK has been formed, a second cover 146 is formed by extruding PEEK over the first cover 144. The third cover 148, comprising ETFE, can then be extruded over the second cover 146. The fourth cover 148, comprising ETFE, can then be extruded over the third cover 148. The composite structure is composed of the first, second, third, and fourth covers 144, 146, 148, 150, respectively, over the conductive element 112a,b,d. The composite structure is formed into a coil shape and then mechanically constrained.

The composite structure can then undergo thermal annealing or stress relieving in a chamber, as previously described. The temperature is raised to about 130° C. to about 210° C. for about 30 seconds to about 30 minutes to allow the polymeric material of PEEK and ETFE to form jacket 130 around conductive element 112a,b,d, after which time the mechanical constraint is removed.

The eighth embodiment listed in Table 1 involves a first cover 144 of PEEK followed by a second cover 146 of FEP. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. After the first cover 144 of PEEK has been formed, a second cover 146 of FEP is introduced over the first cover 144. Second cover 146 can possess a thickness that ranges from about 0.00020 inches to about 0.001 inches. The composite structure, comprised of the first and second covers 144, 146 over the conductive element 112*a,b,d*, is formed into a coil shape and then mechanically constrained.

Thereafter, the composite structure can undergo thermal annealing or stress relieving in a chamber, as previously described. The temperature of the chamber is about 130° C. to about 210° C. for about 30 seconds to about 30 minutes to allow the polymeric material to form jacket 130 over conductive element 112*a,b,d*, after which time the mechanical constraint is removed.

The ninth embodiment listed in Table 1 involves a first cover 144 of PEEK followed by a second cover 146 of PFA. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover of PEEK is formed by extruding the PEEK over a conductive element 112*a,b,d*. After the first cover 144 of PEEK has been formed, a second cover 146 of PFA is introduced over the first cover 144. Second cover 146 can possess a thickness that ranges from about 0.00020 inches to about 0.001 inches. A composite structure is formed of the first and second covers 144, 146 over the conductive element 112*a,b,d*. The composite structure can then undergo thermal annealing or stress relieving in a chamber, as previously described. The temperature is raised to about 130° C. to about 210° C. for about 30 seconds to about 30 minutes to allow the polymeric material to form jacket 130 over conductive element 112*a,b,d*, after which time the mechanical constraint is removed.

The tenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112*a,b,d*. After the first cover 144 of PEEK has been formed, a second cover 146 of ETFE is introduced over the first cover 144 through extrusion or wrapping of ETFE. Second cover 146 can possess a thickness that ranges from about 0.00020 inches to about 0.001 inches. A third cover 148 of FEP is then introduced over second cover 146 through extrusion. Third cover 144 can possess a thickness that ranges from about 0.00020 inches to about 0.001 inches. A composite structure is formed of the first, second, and third covers 144, 146 over the conductive element 112*a,b,d*. The composite structure is formed into a coil shape and then mechanically constrained. In another embodiment, the composite structure is wound on a mandrel coated with a polymer material that can thermally fuse with the outermost cover of the composite structure to mechanically constrain selected regions or the entire coil length. The thermal fuse process can be a lower temperature to effectively fuse without affecting the integrity of the polymer covers.

The composite structure can then undergo thermal annealing or stress relieving in a chamber, as previously described. The temperature in the chamber is about 130° C. to about 210° C. for about 30 seconds to about 30 minutes to allow the polymeric material to form jacket 130 over conductive element 112*a,b,d*, after which time the mechanical constraint is removed.

The eleventh embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. First cover 144 of PEEK is formed by extruding the PEEK over a conductive element 112*a,b,d*. After the first cover 144 of PEEK has been formed, a second cover 146 of ETFE is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112*a,b,d*. The composite structure is formed into a coil shape and then mechanically constrained, as previously described.

The composite structure can then undergo thermal annealing or stress relieving in a chamber. The temperature in the chamber is about 130° C. to about 210° C. for about 30 seconds to about 30 minutes to allow the polymeric material to form jacket 130 around conductive element 112*a,b,d*. Thereafter, the mechanical constraint is removed.

The twelfth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. In one embodiment, the first cover 144 of PEEK is formed by extruding the PEEK over a conductive element 112*a,b,d*. After the first cover 144 of PEEK has been formed, a second cover 146 of ETFE is introduced over the first cover 144. Second cover 146 can possess a thickness of about 0.00020 inches to about 0.001 inches. In another embodiment, second cover 146 can possess a thickness of about 0.00080 inches to about 0.0020 inches. A third cover 148 of EFEP is introduced over the second cover 146 in which the third cover 148 can possess a thickness that ranges from about 0.00020 inches to about 0.001 inches. The composite structure is composed of the first, second, and third covers 144, 146, 148 respectively, over the conductive element 112*a,b,d*. The composite structure is formed into a coil shape and then mechanically constrained and formed, as previously described.

The composite structure can then undergo thermal annealing or stress relieving in a chamber, as previously described. The temperature in the chamber is about 130° C. to about 210° C. for about 30 seconds to about 30 minutes to allow the polymeric material to form jacket 130 to cover conductive element 112*a,b,d*, after which time the mechanical constraint is removed.

The thirteenth embodiment listed in Table 1 involves a first cover 144 of PEEK followed by a second cover 146 of PTFE, which is extruded and nonporous. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. After the first cover 144 of PEEK has been formed, a second cover 146 of PTFE (extruded and nonporous) is introduced over the first cover 144. Second cover 146 can possess a thickness that ranges from about 0.00020 inches to about 0.001 inches. The composite structure, comprised of the first and second covers 144, 146 over the conductive element 112*a,b,d*, is formed into a coil shape and then mechanically constrained.

Thereafter, the composite structure undergoes thermal annealing or stress relieving in a chamber, as previously described. The temperature of the chamber is about 130° C. to about 210° C. for about 30 seconds to about 30 minutes to allow the polymeric material to form jacket 130 over conductive element 112*a,b,d*, after which time the mechanical constraint is removed.

The fourteenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. First cover 144 of PEEK is formed by extruding the PEEK over a conductive element 112*a,b,d*. After the first cover 144 of PEEK has been formed, a second cover 146 of PTFE (extruded and nonporous) is introduced over the first cover 144. Second cover 146 can possess a thickness that ranges from about 0.00020 inches to about 0.001 inches. A third cover 148 of FEP is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112*a,b,d*. The composite structure is formed into a coil shape and then mechanically constrained, as previously described.

The fifteenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. First cover 144 of PEEK is formed by extruding the PEEK over a conductive element 112*a,b,d*. After the first cover 144 of PEEK has been formed, a second cover 146 of PTFE (extruded and nonporous) is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. A composite structure is composed of the first, second, and third covers 144, 146, 148 respectively, over the conductive element 112*a,b,d*. The composite structure is formed into a coil shape and then mechanically constrained, as previously described.

The sixteenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. First cover 144 of PEEK is formed by extruding the PEEK over a conductive element 112*a,b,d*. After the first cover 144 of PEEK has been formed, a second cover 146 of PTFE (extruded and nonporous) is introduced over the first cover 144. Second cover 146 can possess a thickness that ranges from about 0.00020 inches to about 0.001 inches. A third cover 148 of EFEP is introduced over the second cover 146 in which the third cover 148 can possess a thickness that ranges from about 0.00020 inches to about 0.001 inches.

A composite structure is composed of the first, second, and third covers 144, 146, 148 respectively, over the conductive element 112*a,b,d*. The composite structure is formed into a coil shape and then mechanically constrained, as previously described.

The seventeenth embodiment listed in Table 1 involves a first cover 144 of PEEK followed by a second cover 146 of polyurethane. Polyurethane such as polyurethane grade 80A or 55D commercially available from Polymer Technology Group (PTG) located in Berekley, Calif. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.0012 inches. In this embodiment, the first cover of PEEK is formed by extruding the PEEK over a conductive element 112*a,b,d*. After the first cover 144 of PEEK has been formed a second cover 146 of polyurethane is formed by extruding the polyurethane over the first cover 144. Second cover 146 can possess a thickness of about 0.00020 inches to about 0.006 inches. In another embodiment, second cover 146 can possess a thickness that ranges from about 0.0010 inches to about 0.0050 inches. The first and second covers 144, 146 over conductive element 112*a,b,d* is a composite structure. The composite structure is formed into a coil shape and then mechanically constrained, as previously described with the exception of lower temperature being used to form coiled structure without melting the polyurethane i.e. 150° F. or a polyurethane with a melt temperature between 40° C. to 180° C.

The eighteenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112*a,b,d*. After the first cover 144 of PEEK has been formed, a second cover 146 of polyurethane is introduced over the first cover 144. Second cover 146 can possess a thickness that ranges from about 0.00020 inches to about 0.001 inches. In another embodiment, second cover 146 can possess a thickness that ranges from about 0.0010 inches to about 0.0050 inches. A third cover 148 of FEP is extruded over the second cover 146 in which the third cover 148 can possess a thickness that ranges from about 0.00020 inches to about 0.001 inches. The composite structure composed of the first, second, and third covers 144, 146, 148 respectively, is formed into a coil shape and then mechanically constrained.

The composite structure is then thermally annealed over the conductive element 112*a,b,d*. The composite structure is placed into a chamber that possesses a temperature of about 130° C. to about 210° C. for about 30 seconds to about 30 minutes. After the jacket 130 is formed, the mechanical constraint is removed.

The nineteenth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112*a,b,d*. After the first cover 144 of PEEK has been formed, a second cover 146 of polyurethane is introduced over the first cover 144. Second cover 146 can possess a thickness that ranges from about 0.00020 inches to about 0.001 inches. A third cover 148 of PFA is introduced over the second cover 146 in which the third cover 148 can possess a thickness in the range of about 0.00020 inches to about 0.003 inches. The composite structure composed of the first, second, and third covers 144, 146, 148 respectively, is formed into a coil shape and then mechanically constrained.

The composite structure is then thermally annealed to form jacket 130 over the conductive element 112a,b,d. The composite structure is placed into a chamber, in which the temperature is about 130° C. to about 210° C. for about 30 seconds to about 30 minutes. Thereafter, the mechanical constraint is removed.

The twentieth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane is extruded over the first cover 144. Second cover 146 can possess a thickness that ranges from about 0.00020 inches to about 0.001 inches. In another embodiment, second cover 146 can possess a thickness that ranges from about 0.0010 inches to about 0.0050 inches. A third cover 148 of EFEP is introduced over the second cover 146 in which the third cover 148 can possess a thickness that ranges from about 0.00020 inches to about 0.001 inches. EFEP is commercially available from Daikin located in Osaka, Japan. The composite structure composed of the first, second, and third covers 144, 146, 148 respectively, is formed into a coil shape and then mechanically constrained.

The composite structure is then thermally annealed over the conductive element 112a,b,d. The composite structure is placed into a chamber at a temperature of about 130° C. to about 210° C. for about 30 seconds to about 30 minutes. Thereafter, the mechanical constraint is removed.

The twenty first embodiment listed in Table 1 relates to a jacket 130 formed of a first and second covers 144, 146. The twenty first embodiment listed in Table 1 involves a first cover 144 of PEEK followed by a second cover 146 of EFEP. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.002 inches. For this embodiment, the first cover of PEEK is formed by extruding the PEEK over a conductive element 112a,b,d. After the first cover 144 of PEEK has been formed, a second cover 146 of EFEP is introduced over the first cover 144. Second cover 146 can possess a thickness that ranges from about 0.00020 inches to about 0.001 inches. The composite structure is formed into a coil shape and then mechanically constrained.

The composite structure composed of the first and second covers 144, 146 is then thermally annealed over the conductive element 112a,b,d. The composite structure is placed in a chamber with a temperature of about 130° C. to about 210° C. for about 30 seconds to about 30 minutes. Thereafter, the mechanical constraint is removed.

The twenty second embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of polyurethane-silicone copolymers is introduced over the second cover 146 in which the third cover 148 can possess a thickness that ranges from about 0.00020 inches to about 0.003 inches. Polyurethane/silicone block copolymer is, for example, commercially available as polyurethene polydimethyl siloxane copolymer available as pursil from PTG; however, it understood that numerous other trade named products can also be used. The first, second, and third covers 144, 146, 148 over a conductive element 112a,b,d is a composite structure. The composite structure is formed into a coil shape and then mechanically constrained.

The composite structure is then thermally annealed over conductive element 112a,b,d, after which time the mechanical constraint is removed. The composite structure is placed in a chamber with a temperature of about 130° C. to about 210° C. for about 30 seconds to about 30 minutes. Thereafter, the mechanical constraint is removed.

The twenty third embodiment listed in Table 1 relates to a jacket 130 formed of a first, second, third, and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover of PEEK is formed by extruding the PEEK over a conductive element 112a,b,d. After the first cover 144 of PEEK has been formed, a second cover 146 of ETFE is introduced over the first cover 144 through extrusion. Second cover 146 can possess a thickness that ranges from about 0.00020 inches to about 0.001 inches. After the second cover 146 has been formed, a third cover 148 of polyurethane-silicone co-polymers is introduced over the first cover 144. In another embodiment, third cover 148 can possess a thickness that ranges from about 0.0010 inches to about 0.0050 inches. Third cover 148 can possess a thickness that ranges from about 0.00020 inches to about 0.003 inches. After the second cover 146 has been formed, a N cover 150 or fourth cover of FEP is introduced over the third cover 148. N cover 150 can possess a thickness that ranges from about 0.00020 inches to about 0.001 inches. The first, second, third and fourth covers 144, 146, 148, 150 over the conductive element 112a,b,d is a composite structure. The composite structure is formed into a coil shape and then mechanically constrained.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty fourth embodiment listed in Table 1 relates to a jacket 130 formed of a first, second, third, and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. After the second cover 146 has been formed, a third cover 148 of polyurethane-silicone co-polymers is introduced over the first cover 144. Third cover 148 can possess a thickness that ranges from about 0.00020 inches to about 0.001 inches. In another embodiment, the third cover 148 can possess a thickness that ranges from about 0.0010 inches to about 0.0050 inches. After the second cover 146 has been formed, a N cover 152 or fourth cover of PFA is introduced over the third cover 150. N cover 152 can possess a thickness that ranges from about 0.00020 inches to about 0.001 inches. The first, second, third and fourth covers 144, 146, 148, 150 over conductive element 112a,b,d is a composite structure. The composite structure is formed into a coil shape and then mechanically constrained.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty fifth embodiment listed in Table 1 relates to a jacket 130 formed of a first, second, third, and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover of PEEK is formed by extruding the PEEK over a conductive element 112a,b,d. After the first cover 144 of PEEK has been formed, a second cover 146 of ETFE is introduced over the first cover 144. In another embodiment, the second cover 146 can possess a thickness that ranges from about 0.0020 inches to about 0.0030 inches. In yet another embodiment, the second cover 146 can possess a thickness that ranges from about 0.0010 inches to about 0.0050 inches. Second cover 146 can possess a thickness that ranges from about 0.00020 inches to about 0.001 inches. After the second cover 146 has been formed, a third cover 148 of polyurethane-silicone co-polymers is introduced over the first cover 144. Third cover 148 can possess a thickness that ranges from about 0.00020 inches to about 0.001 inches. After the second cover 146 has been formed, a N cover 152 or fourth cover of EFEP is introduced over the third cover 150. N cover 152 can possess a thickness that ranges from about 0.00020 inches to about 0.001 inches. The first, second, third and fourth covers 144, 146, 148, 150 over the conductive element 112a,b,d forms a composite structure. In another embodiment, N cover can possess a thickness that ranges from about 0.0010 inches to about 0.005 inches. The composite structure is formed into a coil shape and then mechanically constrained.

The composite structure is then thermally processed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty sixth embodiment listed in Table 1 relates to a jacket 130 formed of a first, and second covers 144, 146. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers is introduced over the first cover 144. Second cover 146 can possess a thickness that ranges from about 0.00020 inches to about 0.001 inches. In another embodiment, second cover 146 can possess a thickness that ranges from about 0.0010 inches to about 0.0050 inches. The first, and second covers 144, 146, over the conductive element 112a,b,d forms a composite structure. The composite structure is then formed into a coil, as previously described.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty seventh embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers is introduced over the first cover 144. Second cover 146 can possess a thickness that ranges from about 0.00020 inches to about 0.001 inches. In another embodiment, the second cover 146 can possess a thickness that ranges from about 0.0010 inches to about 0.0050 inches. A third cover 148 of FEP is introduced over the second cover 146 in which the third cover 148 can possess a thickness that ranges from about 0.00020 inches to about 0.001 inches. The first, second, and third covers 144, 146, 148 over the conductive element 112a,b,d forms a composite structure. The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty eighth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers is introduced over the first cover 144. Second cover 146 can possess a thickness that ranges from about 0.00020 inches to about 0.001 inches. In another embodiment, the third cover 148 can possess a thickness that ranges from about 0.0010 inches to about 0.0050 inches. A third cover 148 of PFA is introduced over the second cover 146 in which the third cover 148 can possess a thickness that ranges from about 0.00020 inches to about 0.001 inches. The composite structure is formed into a coil shape and then mechanically constrained.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The twenty ninth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers is introduced over the first cover 144. Second cover 146 can possess a thickness that ranges from about 0.00020 inches to about 0.001 inches. In another embodiment, the second cover 146 can possess a thickness that ranges from about 0.0010 inches to about 0.0050 inches. A third cover 148 of EFEP is introduced over the second cover 146 in which the third cover 148 can possess a thickness that ranges from about 0.00020 inches to about 0.001 inches. The composite structure is formed into a coil shape and then mechanically constrained.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirtieth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of polyurethane with surface modifying end groups (SMEs), commercially available as Pellethane® from Dow Chemical in Midland Mich. or as Elasthane™ from PTG located in Berkley, Calif., is introduced over the second cover 146 in which the third cover 148 can possess a thickness that ranges from about 0.00020 inches to about 0.001 inches. In another embodiment, the third cover 148 can possess a thickness that ranges from about 0.0010 inches to about 0.0050 inches. The first, second, and third covers 144, 146, 148 form a composite structure. The composite structure is formed into a coil shape and then mechanically constrained.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty first embodiment listed in Table 1 relates to a jacket 130 formed of a first, second and third covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of polyurethane with SME is introduced over the second cover 146 in which the third cover 148 can possess a thickness that ranges from about 0.00020 inches to about 0.004 inches. In another embodiment, the third cover 148 can possess a thickness that ranges from about 0.0010 inches to about 0.0050 inches. A N or fourth cover 150 of FEP is introduced over the third cover 148 in which the fourth cover 150 possess a thickness of about 0.00020 inches to about 0.001 inches. The first, second, third and fourth covers 144, 146, 148, 150 over conductive element 112a,b,d forms a composite structure.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty second embodiment listed in Table 1 relates to a jacket 130 formed of a first, second and third covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of polyurethane with SME is introduced over the second cover 146 in which the third cover 148 can possess a thickness that ranges from about 0.00020 inches to about 0.001 inches. A N or fourth cover 150 of PFA is introduced over the third cover 148 in which the fourth cover 150 possess a thickness of about 0.00020 inches to about 0.001 inches. The first, second, third and fourth covers 144, 146, 148, 150 over the conductive element 112a,b,d form a composite structure. The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty third embodiment listed in Table 1 relates to a jacket 130 formed of a first, second, third and fourth covers 144, 146, 148, 150, respectively. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of polyurethane with SME is introduced over the second cover 146 in which the third cover 148 can possess a thickness that ranges from about 0.00020 inches to about 0.001 inches. In another embodiment, the third cover 148 can possess a thickness that ranges from about 0.0010 inches to about 0.0050 inches. A N or fourth cover 150 of EFEP is introduced over the third cover 148 in which the fourth cover 150 possess a thickness of about 0.00020 inches to about 0.001 inches. The first, second, third and fourth covers 144, 146, 148, 150 over conductive element 112a,b,d forms a composite structure. The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty fourth embodiment listed in Table 1 relates to a jacket 130 formed of a first, and second covers 144, 146. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane with SME is introduced over the first cover 144. Second cover 146 can possess a thickness that ranges from about 0.00020 inches to about 0.001 inches. The first and second covers 144, 146, over the conductive element 112a,b,d forms the composite structure. The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty fifth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane with SME is introduced over the first cover 144. Second cover 146 can possess a thickness that ranges from about 0.00020 inches to about 0.001 inches. A third cover 148 of FEP is introduced over the second cover 146 in which the third cover 148 can possess a thickness that ranges from about 0.00020 inches to about 0.001 inches. The first, second, and third covers 144, 146, 148 over the conductive element 112a,b,d forms a composite structure.

The composite structure is then thermally annealed to form jacket 130 over conductive element 112a,b,d. The composite structure is placed in a chamber with a temperature for about 130° C. to about 210° C. for about 30 seconds to about 30 minutes. Thereafter, the mechanical constraint is removed.

The thirty sixth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane with SME is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The thirty seventh embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane with SME is introduced over the first cover 144. Second cover 146 can possess a thickness that ranges from about 0.00020 inches to about 0.001 inches. A third cover 148 of EFEP is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The thirty eighth embodiment listed in Table 1 relates to a jacket 130 formed of a first, and second covers 144, 146. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers with SME is introduced over the first cover 144. Second cover 146 can possess a thickness that ranges from about 0.00020 inches to about 0.001 inches. The first, and second covers 144, 146 are then thermally annealed to form jacket 130 over conductive element 112a,b,d, after which time the mechanical constraint is removed.

The thirty ninth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers with SME is introduced over the first cover 144. Second cover 146 can possess a thickness that ranges from about 0.00020 inches to about 0.001 inches. A third cover 148 of FEP is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The fortieth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers with SME is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty first embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyurethane-silicone copolymers with SME is introduced over the first cover 144. Second cover 146 can possess a thickness that ranges from about 0.00020 inches to about 0.001 inches. A third cover 148 of EFEP is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty second embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of silicone is then introduced over second cover 146. Third cover 144 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty third embodiment listed in Table 1 relates to a jacket 130 formed of a first, second, third and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of silicone is introduced over the second cover 146 in which the third cover 148 can possess a thickness that ranges from about 0.00020 inches to about 0.001 inches. A fourth cover 150 of FEP is introduced over the second cover 146 in which the fourth cover 150 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty fourth embodiment listed in Table 1 relates to a jacket 130 formed of a first, second, third and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of silicone is introduced over the second cover 146 in which the third cover 148 can possess a thickness that ranges from about 0.00020 inches to about 0.001 inches. A fourth cover 148 of PFA is introduced over the second cover 146 in which the third cover 148 can possess a thickness that ranges from about 0.00020 inches to about 0.001 inches. The first, second, third and fourth covers 144, 146, 148, 150 are then thermally annealed to form jacket 130 over conductive element 112a,b,d, after which time the mechanical constraint is removed.

The forty fifth embodiment listed in Table 1 relates to a jacket 130 formed of a first, second, third and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of ETFE is introduced over the first cover 144. Second cover 146 can possess a thickness that ranges from about 0.00020 inches to about 0.001 inches. A third cover 148 of silicone is introduced over the second cover 146 in which the third cover 148 can possess a thickness that ranges from about 0.00020 inches to about 0.001 inches. A fourth cover 150 of EFEP is introduced over the third cover 148 in which the fourth cover 150 can possess a thickness that ranges from about 0.00020 inches to about 0.001 inches. The first, second, third and fourth covers 144, 146, 148, 150 are then thermally annealed to form jacket 130 over conductive element 112a,b,d, after which time the mechanical constraint is removed.

The forty sixth embodiment listed in Table 1 relates to a jacket 130 formed of a first, and second covers 144, 146. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of silicone is introduced over the first cover 144. Second cover 146 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty seventh embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of silicone is introduced over the first cover 144. Second cover 146 can possess a thickness that ranges from about 0.00020 inches to about 0.001 inches. A third cover 148 of FEP is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty eighth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of silicone is introduced over the first cover 144. Second cover 146 can possess a thickness that ranges from about 0.00020 inches to about 0.001 inches. A third cover 148 of PFA is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The forty ninth embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of silicone is introduced over the first cover 144. Second cover 146 can possess a thickness that ranges from about 0.00020 inches to about 0.001 inches. A third cover 148 of EFEP is introduced over the second cover 146 in which the third cover 148 can possess a thickness that ranges from about 0.00020 inches to about 0.001 inches. The first, second, and third covers 144, 146, 148 are then thermally annealed to form jacket 130 over conductive element 112a,b,d, after which time the mechanical constraint is removed.

The fiftieth embodiment listed in Table 1 relates to a jacket 130 formed of a first, and second covers 144, 146. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of polyvinylidene fluoride (PVDF) is introduced over the first cover 144. Second cover 146 can possess a thickness that ranges from about 0.00020 inches to about 0.001 inches. The first, and second covers 144, 146 are then thermally annealed to form jacket 130 over conductive element 112a,b,d, after which time the mechanical constraint is removed.

The fifty first embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of PEEK is introduced over the first cover 144. Second cover 146 can possess a thickness that ranges from about 0.00020 inches to about 0.001 inches. A third cover 148 of PVDF is introduced over the second cover 146 in which the third cover 148 can possess a thickness that ranges from about 0.00020 inches to about 0.001 inches. The first and second covers 144, 146 are then thermally annealed to form jacket 130 over conductive element 112a,b,d.

The fifty second embodiment listed in Table 1 relates to a jacket 130 formed of a first, second, third and fourth covers 144, 146, 148, 150. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of PEEK is extruded over the first cover 144. Second cover 146 can possess a thickness that ranges from about 0.00020 inches to about 0.001 inches. A third cover 148 of PVDF is introduced over the second cover 146 in which the third cover 148 can possess a thickness that ranges from about 0.00020 inches to about 0.001 inches. A fourth cover 150 of PVDF is introduced over the third cover 148 in which the fourth cover 150 can possess a thickness that ranges from about 0.00020 inches to about 0.001 inches. The first, second, third and fourth covers 144, 146, 148, 150 are then thermally processed (e.g. annealed etc.) to form jacket 130 over conductive element 112a,b,d, after which time the mechanical constraint is removed.

The fifty third embodiment listed in Table 1 relates to a jacket 130 formed of a first, second and third covers 144, 146, 148. First cover 144 of PEEK can possess a thickness that ranges from about 0.0005 inches to about 0.0015 inches of extruded PEEK. In another embodiment, first cover 144 can possess a thickness that ranges from about 0.00020 inches to about 0.001 inches. For this embodiment, the first cover 144 of PEEK is formed by extruding the PEEK over a conductive element 112a,b,d. After the first cover 144 of PEEK has been formed, a second cover 146 of PVDF is extruded over the first cover 144. Second cover 146 can possess a thickness that ranges from about 0.00020 inches to about 0.001 inches. A third cover 148 of PVDF is introduced over the second cover 146 in which the third cover 148 can possess a thickness that ranges from about 0.00020 inches to about 0.001 inches. The first and second covers 144, 146 are then thermally annealed to form jacket 130 over conductive element 112a,b,d.

Table 1, presented below, summarizes the various embodiments of jacket 130.

TABLE 1

Embodiments of jacket 130 that comprise one or more polymeric compounds

| No. | First Cover | Second Cover | Third Cover | N Cover |
|---|---|---|---|---|
| 1 | PEEK | | | |
| 2 | PEEK | PEEK | | |
| 3 | PEEK | PEEK | PEEK | |
| 4 | PEEK | ETFE | | |
| 5 | PEEK | PEEK | ETFE | |
| 6 | PEEK | PEEK | PEEK | ETFE |
| 7 | PEEK | PEEK | ETFE | ETFE |
| 8 | PEEK | FEP | | |
| 9 | PEEK | PFA | | |
| 10 | PEEK | ETFE | FEP | |
| 11 | PEEK | ETFE | PFA | |
| 12 | PEEK | ETFE | EFEP | |
| 13 | PEEK | PTFE (extruded, nonporous) | | |
| 14 | PEEK | PTFE (extruded, nonporous) | FEP | |
| 15 | PEEK | PTFE (extruded, nonporous) | PFA | |
| 16 | PEEK | PTFE (extruded, nonporous) | EFEP | |
| 17 | PEEK | Polyurethane | | |

TABLE 1-continued

Embodiments of jacket 130 that comprise one or more polymeric compounds

| No. | First Cover | Second Cover | Third Cover | N Cover |
|---|---|---|---|---|
| 18 | PEEK | Polyurethane | FEP | |
| 19 | PEEK | Polyurethane | PFA | |
| 20 | PEEK | Polyurethane | EFEP | |
| 21 | PEEK | EFEP | | |
| 22 | PEEK | ETFE | Polyurethane-silicone copolymers | |
| 23 | PEEK | ETFE | Polyurethane-silicone copolymers | FEP |
| 24 | PEEK | ETFE | Polyurethane-silicone copolymers | PFA |
| 25 | PEEK | ETFE | Polyurethane-silicone copolymers | EFEP |
| 26 | PEEK | Polyurethane-silicone copolymers | | |
| 27 | PEEK | Polyurethane-silicone copolymers | FEP | |
| 28 | PEEK | Polyurethane-silicone copolymers | PFA | |
| 29 | PEEK | Polyurethane-silicone copolymers | EFEP | |
| 30 | PEEK | ETFE | Polyurethane with SME | |
| 31 | PEEK | ETFE | Polyurethane with SME | FEP |
| 32 | PEEK | ETFE | Polyurethane with SME | PFA |
| 33 | PEEK | ETFE | Polyurethane with SME | EFEP |
| 34 | PEEK | Polyurethane with SME | | |
| 35 | PEEK | Polyurethane with SME | FEP | |
| 36 | PEEK | Polyurethane with SME | PFA | |
| 37 | PEEK | Polyurethane with SME | EFEP | |
| 38 | PEEK | Polyurethane-silicone copolymers with SME | | |
| 39 | PEEK | Polyurethane-silicone copolymers with SME | FEP | |
| 40 | PEEK | Polyurethane-silicone co-polymers with SME | PFA | |
| 41 | PEEK | Polyurethane-silicone co-polymers with SME | EFEP | |
| 42 | PEEK | ETFE | Silicones | |
| 43 | PEEK | ETFE | Silicones | FEP |
| 44 | PEEK | ETFE | Silicones | PFA |
| 45 | PEEK | ETFE | Silicones | EFEP |
| 46 | PEEK | Silicones | | |
| 47 | PEEK | Silicones | FEP | |
| 48 | PEEK | Silicones | PFA | |
| 49 | PEEK | Silicones | EFEP | |
| 50 | PEEK | PVDF | | |
| 51 | PEEK | PEEK | PVDF | |
| 52 | PEEK | PEEK | PVDF | PVDF |
| 53 | PEEK | PVDF | PVDF | |

The insulated conductive element formed through jacket 130 over conductive element 112a,b,d can be helically wrapped around a mandrel (not shown). After winding the insulated cable onto the mandrel and mechanically restraining this composite structure, the polymeric material over the conductive element (e.g. cable etc.) can be annealed to minimize springback and allow the conductive element (e.g. cable etc.) to retain its coiled shape. After being removed from the mandrel, the conductive element (e.g. cable etc.) retains its coiled shape.

Figure 5A:
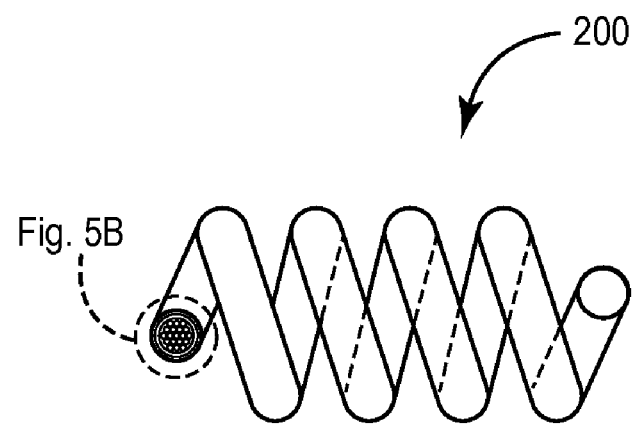
FIG. 5A is a schematic view of an exemplary insulated conductive element.
Figure 5B:
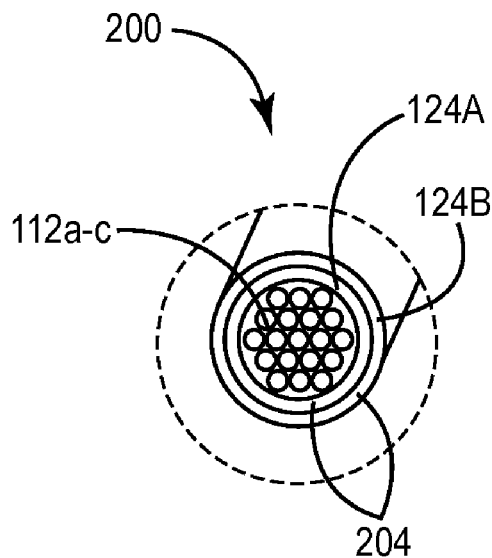
FIG. 5B is a cross-sectional view of the insulated conductive element depicted in FIG. 5A.

Insulated conductive element 200 is depicted in FIGS. 5A-5B. Insulated conductive element 200 includes a conductive element 112a,b,d (i.e. cable, coiled cable etc.) with a thin polymeric material 204 or cover that has been thermally processed (e.g. annealed etc.) to conductive element 112a,b,d. Polymeric material 204 comprises a first and second covers 124a,124b. Conductive element 112a,b,d has an outer diameter of about 0.09 inches or less. In one embodiment, conductive element 112a,b,d can be a 1×19 cable construction with filaments composed of MP35N/Ag core.

Figure 6A:
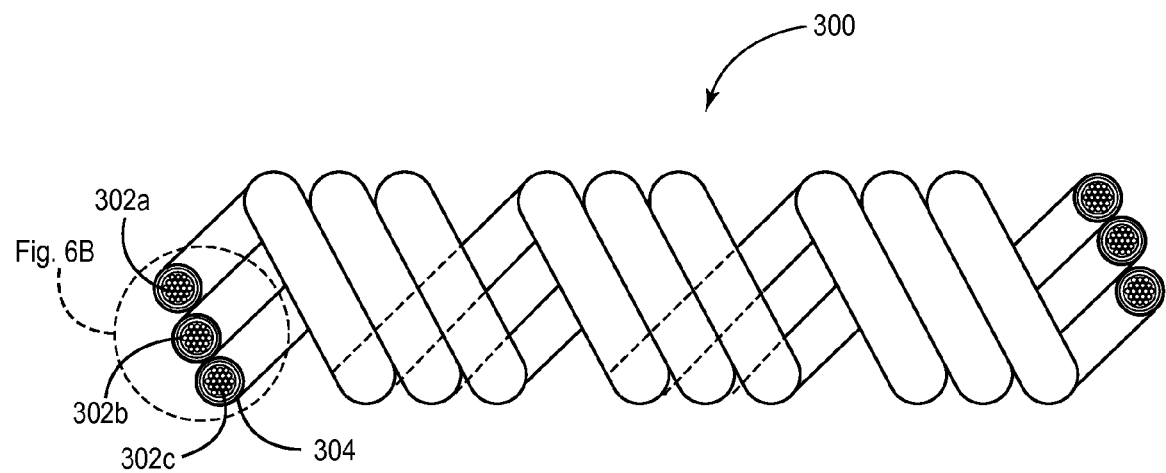
FIG. 6A is a schematic view of an exemplary insulated multi-conductor element.
Figure 6B:
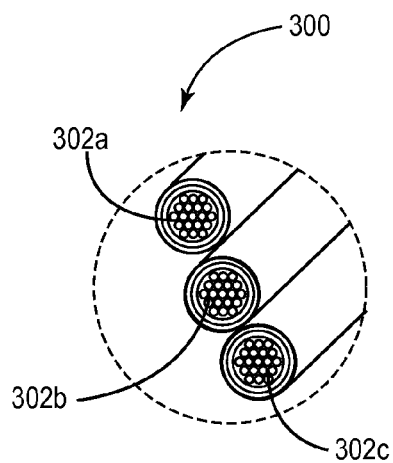
FIG. 6B is a schematic cross-sectional view of an exemplary insulated multi-conductor element depicted in FIG. 6A.

Referring to FIGS. 6A-6B, an insulated conductive element 300 is depicted that comprises a set of conductors 302a-c (i.e. three conductors) and an insulative layer or cover 304. Conductive element 300 such as a 1×19 cable MP35N/Ag core and has an outer diameter of about 0.055 inches. Insulative layer 304 comprises a layer of PEEK and a layer of ETFE. In one embodiment, each layer of PEEK and ETFE is about 0.0008 inches or less. In another embodiment, each layer of PEEK and ETFE is about 0.002 inches or less.

Figure 7A:
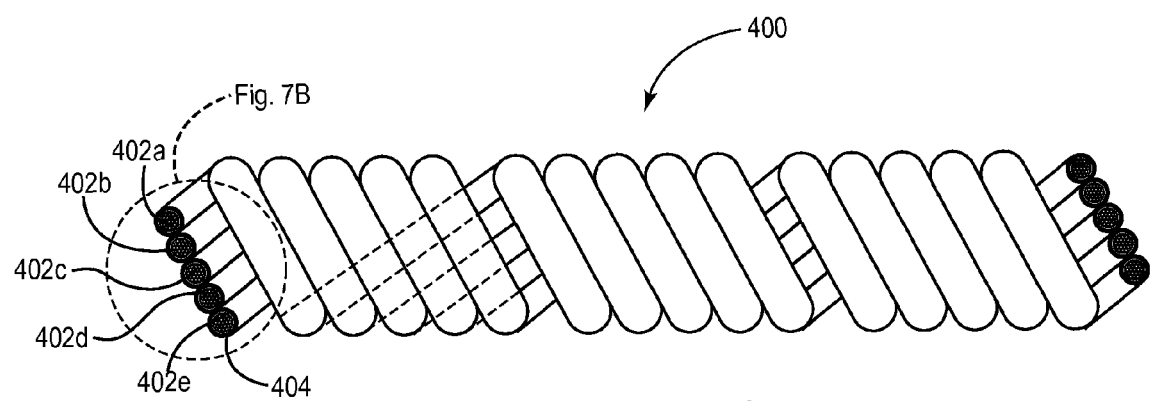
FIG. 7A is a schematic view of another exemplary insulated multi-conductor element.
Figure 7B:
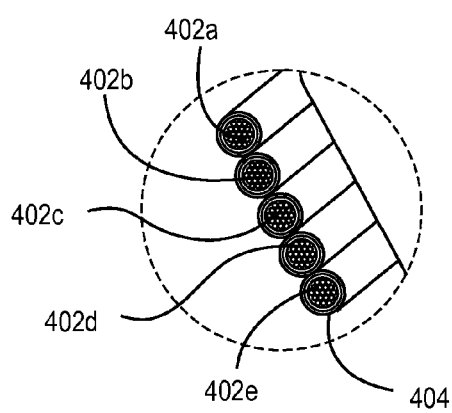
FIG. 7B is a schematic cross-sectional view of an exemplary insulated multi-conductor element depicted in FIG. 7A.

Referring to FIG. 7A-7B, insulated conductive element 400 comprises a set of conductors 402a-e (i.e. five conductors) and an insulative layer or cover 404. Conductive element 400 has an outer diameter of about 0.060 inches and is a 1×19 cable. Insulative layer 404 comprises a layer of PEEK and a layer of ETFE. In one embodiment, each layer of PEEK and ETFE is about 0.0008 inches or less. In another embodiment, each layer of PEEK and ETFE is about 0.002 inches or less.

Figure 8A:
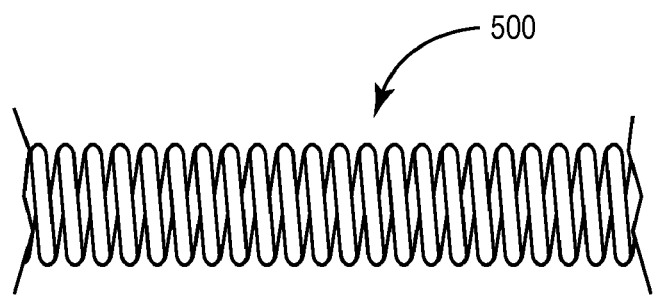
FIG. 8A is a schematic view of an exemplary insulated multi-conductor element before its stretched.
Figure 8B:
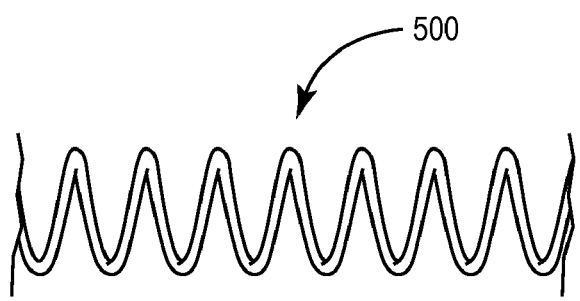
FIG. 8B is a schematic view of an exemplary insulated multi-conductor element being stretched.
Figure 8C:
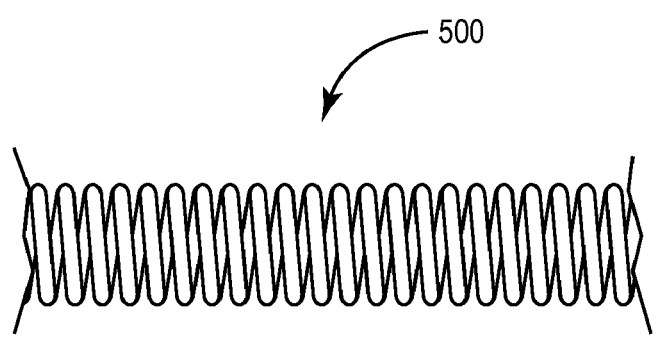
FIG. 8C is an exemplary insulated multi-conductor element in a relaxed position and returning to its original coiled shape.

Referring to FIGS. 8A-8C, jacketed conductive element 500 is shown as retaining its coiled shape despite being stretched. Conductive element 500 comprises a 1×19 cable construction with filaments composed of MP35N/Ag core with an insulative or jacketed layer, coating or cover. The insulative layer comprises a layer of PEEK and a layer of ETFE. In one embodiment, each layer of PEEK and ETFE is about 0.0008 inches or less. In one embodiment, each layer of PEEK and ETFE is about 0.002 inches or less. Referring to FIG. 8A, insulated conductive element 500 is depicted in a relaxed position (FIG. 8A) over a mandrel. While over the mandrel, conductive element 500 is thermally annealed. Referring to FIG. 8B, insulated conductive element 500 is depicted in a stretched position. Thereafter, insulated conductive element 500 moves to a relaxed position after being stretched (FIG. 8C). The insulated conductive element 500 retains 99% or more of its original coiled shape. In another embodiment, insulated conductive element 500 comprises 95% or more of its original coiled shape.

Figure 9:
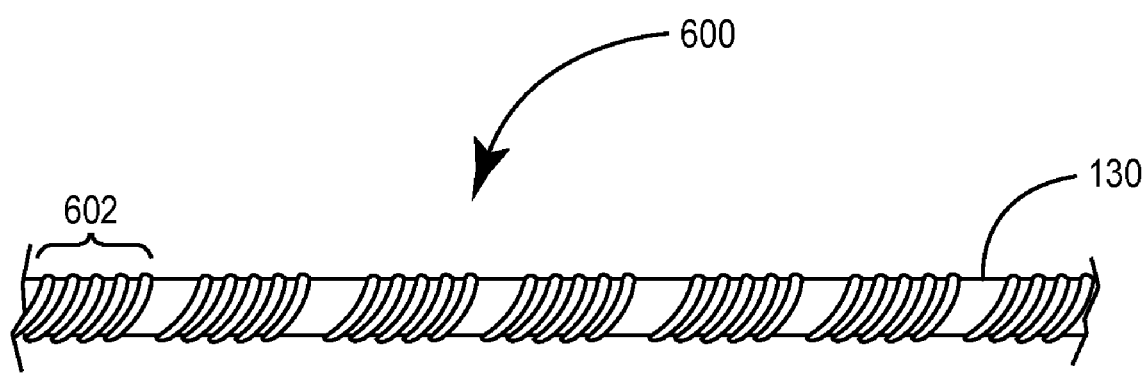
FIG. 9 is a schematic view of an exemplary insulated multi-conductor element wrapped around a tubular insulative element or a coil liner.
Figure 10A:
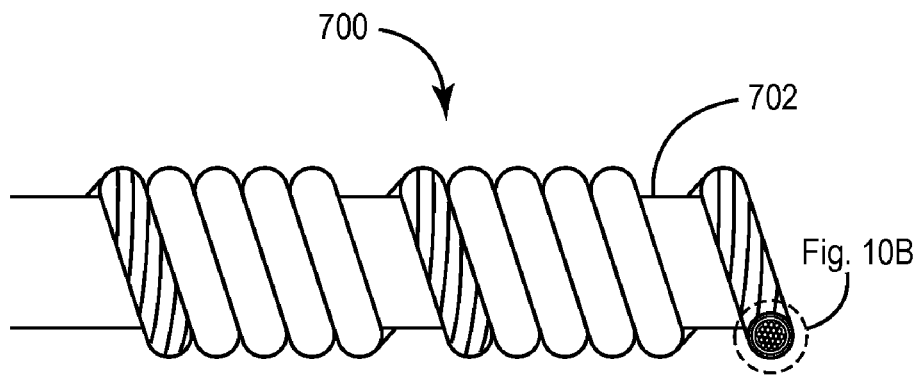
FIG. 10A is a schematic view of yet another exemplary insulated multi-conductor element wrapped around a mandrel.
Figure 10B:
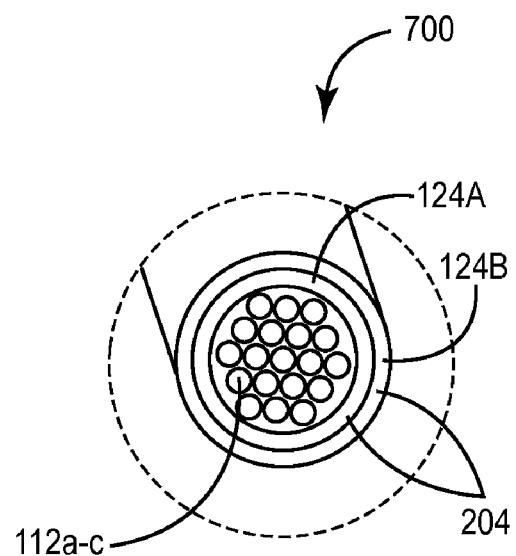
FIG. 10B is a cross-sectional view of the insulated conductive element depicted in FIG. 10A.

Referring to FIG. 9, insulated conductive element 600 is helically wrapped around a coil liner 130. Insulated conductive element 600 comprises a set of jacketed conductors 602 (i.e. five conductors cable-coil). Referring to FIG. 10A-10B, insulated conductive element 700 is helically wrapped around a mandrel 702. Insulated conductive element 700 comprises a set of conductors 702 (i.e. five conductors) and an insulative layer or cover.

Figure 11:
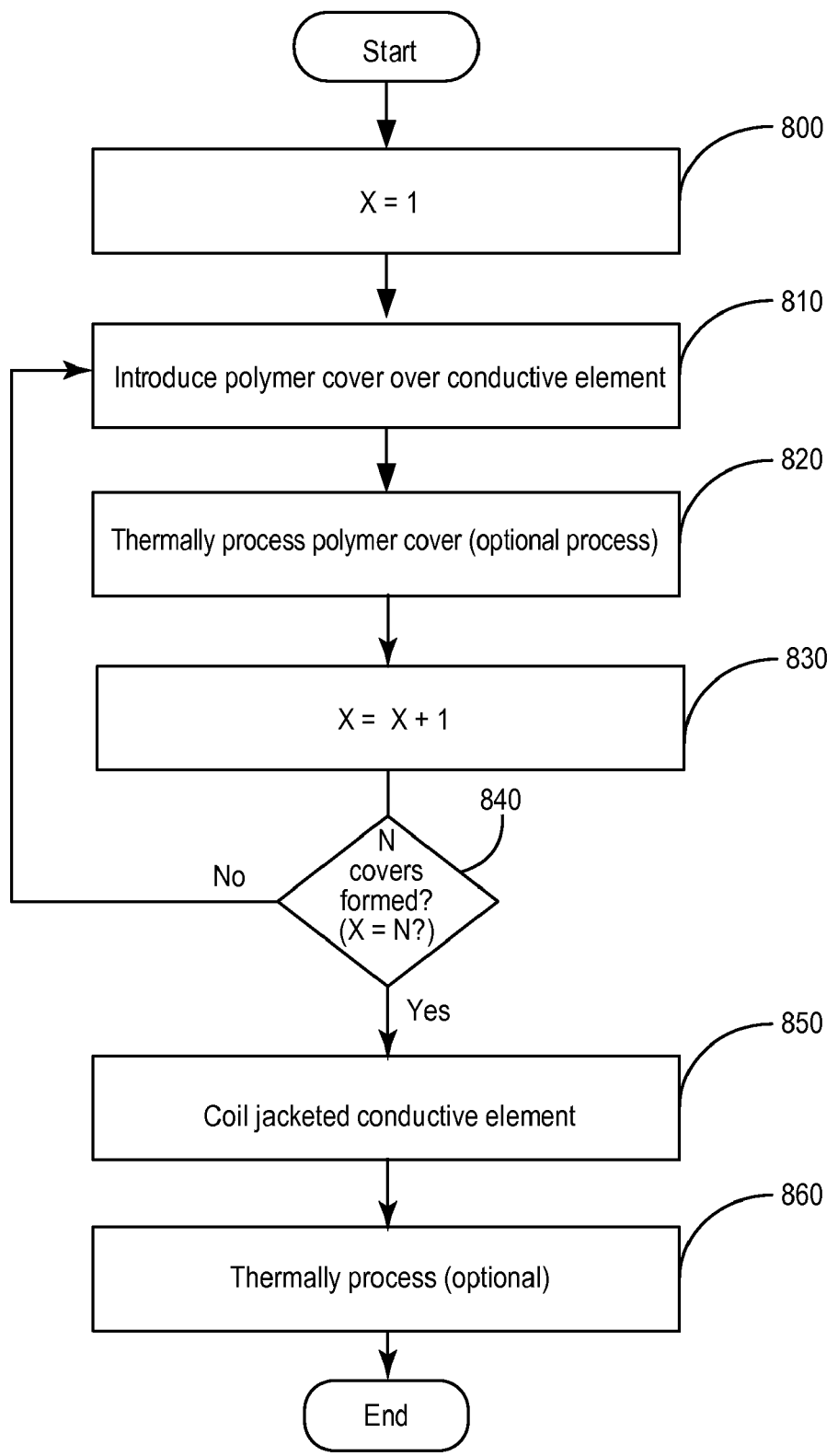
FIG. 11 is a flow diagram for forming a coiled jacketed conductive element.

FIG. 11 is a flow diagram of an exemplary computer-implemented method or a manual process to form at least one cover of PEEK over the conductive element. At block 800, a counter, x, is initiated to 1 in order to count the number polymer covers formed over a conductive element. At block 810, a polymer is extruded (also referred to as introduced) over the conductive element. Polymers with high elastic modulus (i.e. stiffness) such as PEEK are preferred since PEEK can be annealed or stress relieved to increase crystallinity and set the coil shape in conductive element 112a-c. At block 820, the polymer cover can undergo an optional thermal process.

At block 830, the counter, X, is incremented by adding 1 to the previous value of X. At block 840, a determination is made as to whether a sufficient number of polymer covers have been formed over the conductive element. In this embodiment, a determination is made as to whether X=N where N equals the number of pre-selected covers to be added to the conductive element. If X does not equal N, the process control returns to block 810 to extrude the same or different polymer over the previous polymer cover. If x does equal N, then the process goes to block 850, where the jacketed conductive element undergoes coiling, as previously described. If x does not equal N, the process returns to introducing another polymeric cover over the conductive element 112a-d. If x does equal N, no additional polymer covers are introduced over the conductive element 112a-d. At block 850, the jacketed conductive element is formed into a coil. At block 860, the coiled jacketed conductive element can undergo an optional thermal process. If the method is implemented on a computer, the number of polymeric covers formed over the conductive element and/or the types of polymeric material used for each cover can be displayed on a graphical user interface of a computer. The computer-implemented instructions are executed on a processor of a computer.

Numerous alternative embodiments can be implemented using the principles described herein. In one embodiment, the single cover of PEEK may be introduced or applied directly over a mandrel (not shown) through extrusion. A mandrel is a cylindrically shaped body with an outer diameter that ranges from about 10 mil to about 30 mil; however, it is to be appreciated that the range can be modified depending upon the desired coil diameter. The mandrel is coated with a material to easily release a jacket 130 formed from a polymeric compound. PEEK covers the mandrel which forms a jacket 130 with an inner lumen that possesses about the same or similar ranges as the outer diameter of the mandrel. After jacket 130 can then be strung through a lumen of another jacket 130.

Additionally, while an extrusion process can produce a continuous longitudinal tube, PEEK can also be extruded into sheets that could be laminated with an adhesive (e.g. ETFE, FEP, PFA, EFEP etc.) and slit into rolls of tape which could subsequently be wrapped on an mandrel, cable etc. to produce multilayer insulation tubes or "covers".

PEEK can also be molded instead of extruded. Optionally, a secondary machining process could be used to drill-out or otherwise produce a lumen to form the longitudinal tube. Filaments of PEEK can be used to produce high strength mono or multi-filament fibers, e.g. for a "tensile lock" feature in the lumen of a coil. Filaments of PEEK can also be used to produce braids or other reinforcing structures. In yet another embodiment, an adhesive (e.g. FEP etc.) (not shown) is placed between one or more covers 144, 146, 148, 150, 152.

In another embodiment, the single cover or first cover of PEEK can be introduced or applied directly over a conductive element 112a,b,d through, for example, a multiple-layer tape wrapping or other film wrapping process, using a suitable adhesive or thermal bonding process to enable coupling between each layer of tape or film.

In one embodiment, PEEK may be extruded or wrapped over a mandrel. Jacket 130 is then removed from the mandrel. A jacket 130 that comprises PEEK can be used to house a conductive element 112c, a delivery device (e.g. stylet, guidewire etc.) or another suitable device. If jacket houses a conductive element 112a-c, the conductive element 112c is inserted into jacket 130. The insulated conductive element is then wrapped around the polymeric porous layer of the mandrel. In one embodiment, the conductive element is helically wrapped around the mandrel. In one embodiment, a jacketed conductive element that is not coiled and shape set, i.e. the coil liner, can still undergo a thermal process such as annealing process to increase crystallinity and resulting mechanical properties.

In another embodiment for constraining coiled conductive element 112a, b,d, the coiled conductive element 112a, b,d can be mechanically constrained by adhesively bonding the proximal and distal ends of the cable filars to each other or to the mandrel itself. Exemplary adhesive can include silicones, urethanes, flouropolymers etc. Selectively adhesively bonding between filars of a coiled conductive element 112a,b,d and/or to the mandrel itself can include placing adhesives at certain points along the conductive element 112a,b,d or a continuous path along the conductive element 112a,b,d. It can be appreciated that adhesives used could include those activated via thermal, UV light, chemical and solvent-based methods.

In another embodiment, selectively adhesively bonding coiled conductive element 112a,b,d (i.e. covered cable filars) to a polymeric coated mandrel (e.g. a silver plated copper mandrel or wire). The polymer selected for the mandrel can be selected from Table 1. The coating on the mandrel can form the inner insulation or coil liner. There are also numerous embodiments related to mechanically constraining the coil during subsequent processing or bonding the coiled conductive element 112 or coiled conductor to the mandrel. For example, the outermost insulation (ETFE, Silicone, Pursil, Pur or combination thereof) on a mandrel, can be wound to adhere the coil or conductive element 112a-d to the mandrel on ends or in select regions. Heat processing can then be applied to help the coil composite structure to form a more permanent or stable coiled shape.

In yet another embodiment, the coiled cable mandrel assembly is placed into an overlay tubing and then released. This embodiment reduces diametric expansion that may occur with coil springback. Additionally, each polyurethane embodiment listed in Table 1 can have a cover thickness that ranges from about 0.001 to about 0.005 inches. It can be appreciated that in all embodiments which employ an outermost polymer cover that has a lower melting point than PEEK, thermal fusing of the composite coiled structure (i.e. coated cable filars) can be accomplished at lower temperatures (such as at, or near, the melting point such as within 10 degrees ° F. of the melting point for the outermost polymer cover. This approach can result in mechanically constraining selective regions along conductors 112 a,b,d. These lower temperatures can be used to effectively fuse filars to each other thereby affecting the integrity of the PEEK and other covers with relatively high melting points.

In another embodiment, coils can be formed without a mandrel using wire guide equipment, commercially available from Simco Spring Machinery Company located in Tapei, Taiwan. While at least one exemplary embodiment has been presented in the foregoing detailed description of the invention, it should be appreciated that a vast number of variations exist. For example, the conductive element 112c such as the inner coil filars, depicted in FIG. 3A, can be jacketed. Listed below are related U.S. patent applications that describe various improvements to the methods and devices of the invention described herein. Each of these patent applications are incorporated by reference in their entirety.

Co-pending U.S. patent application Ser. No. 12/211,093 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

Co-pending U.S. patent application Ser. No. 12/211,070 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

Co-pending U.S. patent application Ser. No. 12/211,092 entitled "MEDICAL ELECTRICAL LEAD" filed by Gregory A. Boser and Kevin R. Seifert and assigned to the same Assignee as the present invention. This co-pending application is hereby incorporated herein by reference in its entirety.

The description of the invention is merely exemplary in nature and, thus, variations that do not depart from the gist of the invention are intended to be within the scope of the invention. Such variations are not to be regarded as a departure from the spirit and scope of the invention.

The invention claimed is:

1. A method of insulating a conductive element in a medical electrical lead comprising the ordered steps of:
   introducing a polymeric material over at least one conductive element;
   wrapping helically the at least one conductive element around a mandrel; and then
   while the at least one conductive element is wrapped around the mandrel, coupling the polymeric material over the at least one conductive element and thereby setting a coiled shape in the conductive element; and
   wherein coupling the polymeric material over the at least one conductive element includes shape setting the polymeric material and then thermally bonding a lower melting point second polymeric material previously introduced over a first polymeric material.

2. The method of claim 1, wherein coupling the polymeric material over the at least one conductive element includes adhesively bonding the polymeric material to an underlying structure.

3. The method of claim 1, wherein coupling the polymeric material over the at least one conductive element includes thermally bonding selectively at points along a length of an assembled structure.

4. The method of claim 1, wherein coupling the polymeric material over the at least one conductive element includes adhesively bonding selectively at points along a length of an assembled structure.

5. The method of claim 1, wherein the second polymeric material is of a lower strength and lower elongation than the first polymeric material.

6. The method of claim 1, wherein the first and the second polymeric materials are coupled with a weakly bonded interface.

7. The method of claim 1, wherein the first polymeric material is treated to promote a weakly bonded interface when coupled to the second polymeric material.

8. The method of claim 7, wherein treated to promote a weakly bonded interface includes one of plasma and a chemical treatment.

9. The method of claim 1, wherein coupling includes mechanically constraining the at least one conductive element with one of an outer tubular material and a component.

* * * * *